United States Patent
Thomas

(10) Patent No.: US 7,848,732 B2
(45) Date of Patent: Dec. 7, 2010

(54) MOBILE COMMUNICATIONS DEVICES INCLUDING ENVIRONMENTAL HAZARD MONITORING

(75) Inventor: Robert P. Thomas, Cumming, GA (US)

(73) Assignee: AT&T Intellectual Property I, L.P., Reno, NV (US)

( * ) Notice: Subject to any disclaimer, the term of this patent is extended or adjusted under 35 U.S.C. 154(b) by 678 days.

(21) Appl. No.: 11/782,193

(22) Filed: Jul. 24, 2007

(65) Prior Publication Data

US 2009/0029716 A1    Jan. 29, 2009

(51) Int. Cl.
*H04M 11/04*    (2006.01)
(52) U.S. Cl. .............. 455/404.1; 455/404.2; 455/456.1; 455/556.1
(58) Field of Classification Search ............... 455/404.1, 455/404.2, 456.1, 556.1
See application file for complete search history.

(56) References Cited

U.S. PATENT DOCUMENTS

| 6,703,930 B2 | 3/2004 | Skinner |
| 6,741,174 B2 | 5/2004 | Rhoades |
| 2006/0265195 A1* | 11/2006 | Woodard et al. ............ 702/188 |
| 2007/0087726 A1* | 4/2007 | McGary et al. .......... 455/404.1 |

OTHER PUBLICATIONS

Carbon Monoxide Sensor, Sensors & Transducers e-Digest, vol. 67, Issue 5, May 2006: Product News, accessed from http://www.sensorsportal.com.
David Murphy, "Homeland Security's Latest Poison-Sniffer: Your Cell Phone," PCMag.com, Apr. 10, 2010, <http://www.pcmag.com/article2/0,2817,2362483,00.asp>.

* cited by examiner

*Primary Examiner*—Barry W Taylor
(74) *Attorney, Agent, or Firm*—Moazzam & Associates, LLC

(57) ABSTRACT

Mobile communications devices include sensors for monitoring for environmental hazards that an individual carrying the mobile communications device may encounter when moving from place to place. Examples of such environmental hazards are smoke, poisonous gases including carbon monoxide, and the like. Upon detecting an environmental hazard, the mobile communications device of the individual may take some action. The mobile communications device may generate a local alert to call the attention of the individual to the environmental hazard. The mobile communications device may originate an outbound emergency communication to inform other parties such as emergency personnel that the environmental hazard exists.

16 Claims, 4 Drawing Sheets

MOBILE COMMUNICATIONS DEVICES INCLUDING ENVIRONMENTAL HAZARD MONITORING

TECHNICAL FIELD

Embodiments relate to mobile communications devices. More particularly, embodiments relate to mobile communications device that monitor for environmental hazards.

BACKGROUND

Environmental hazards such as poisonous gases including carbon monoxide and smoke lead to significant numbers of fatalities each year. These hazards may not be readily observable by those in danger. Fixed monitors may be placed in locations where individuals might be exposed to such hazards to detect the hazard and alert the individuals to the danger. However, there may be no requirement, either in public or private locations, that such monitors be installed, and individuals may be unnecessarily put at risk. Furthermore, individuals may not know whether such monitors are in place and therefore, may not know that they are at risk.

Mobile communications devices such as cellular telephones, mobile Internet devices, personal daily assistant devices, and the like are becoming ubiquitous devices. Furthermore, mobile communications networks provide mobile communications service to most populated areas of many countries. Thus, it is possible, if not likely, that individuals being exposed to environmental hazards are carrying a mobile communications device. However, mobile communications devices merely give the individual the ability to report an environmental hazard that has been detected by some other means. If the individual is not alerted to an otherwise undetectable hazard, then the user may remain unaware of the hazard, and the mobile communications device will be of no assistance.

SUMMARY

Embodiments provide for mobile communications devices that include monitoring of environmental hazards. The mobile communications devices may detect the presence of an environmental hazard and may perform one or more various acts in response to the hazard. The mobile communications device of one or more embodiments may provide a local alert to the individual carrying the mobile communications device, such as by sounding an alarm, blinking a light or a display screen, creating vibrations, and so forth. The mobile communications device of one or more embodiments may originate an outbound call to one or more emergency numbers and may provide stored information during the outbound call, such as an announcement of the location and/or the hazard being detected.

Embodiments include a mobile communications device that includes a transceiver within the portable body that sends and receives wireless communication signals to a mobile communications network. The mobile communications device further includes an environmental hazard sensor within the portable body that produces a signal value based on sensing at least one characteristic of an environmental hazard. A processor interacts with the transceiver to establish communications with the mobile communications network and interacts with the environmental hazard sensor to analyze the signal value against a reference and to originate an outbound communication to the mobile communications network upon detecting that the signal value exceeds the reference. Additionally, a portable power source is affixed to the portable body and provides electrical power to the transceiver, the environmental sensor, and the processor.

Embodiments include a method of alerting to a hazardous environment using a mobile communications device present within the hazardous environment. The method involves producing via an environmental hazard sensor within the mobile communications device a signal value and determining via the mobile communications device whether to originate an outbound communication to the mobile communications network on the basis of the signal value. The method further involves originating the outbound communication from the mobile communications device when it is determined to be appropriate and providing information stored at the mobile communications device regarding a location of the hazardous environment during the outbound communication.

Embodiments include a computer readable medium containing instructions encoded thereon that perform acts that include producing via an environmental hazard sensor within a mobile communications device a signal value. The acts further include determining via the mobile communications device whether to generate an alarm on the basis of the signal value and determining whether to originate an outbound communication to a mobile communications network if no acknowledgement to the alarm is received at the mobile communications device within a set period of time. The acts also include originating the outbound communication from the mobile communications device to the mobile communications network upon determining that no acknowledgement has been received at the mobile communications device within the set period of time.

Other systems, methods, and/or computer program products according to embodiments will be or become apparent to one with skill in the art upon review of the following drawings and detailed description. It is intended that all such additional systems, methods, and/or computer program products be included within this description, be within the scope of the present invention, and be protected by the accompanying claims.

DETAILED DESCRIPTION

Embodiments provide for mobile communications devices that monitor for environmental hazards in the presence of the individual carrying the mobile communications device. The mobile communications may take one or more actions without user intervention upon detecting that the hazard exists.

For example, the mobile communications device may produce local alarms to draw the attention of the individual to the potential danger. As another example, the mobile communications device may originate an outbound call to report the hazard to an emergency contact, such as 911 emergency services and/or relatives and friends of the individual. In other examples, the mobile communications device may offer both local alarms and origination of outbound calls to report the hazard.

Figure 1:
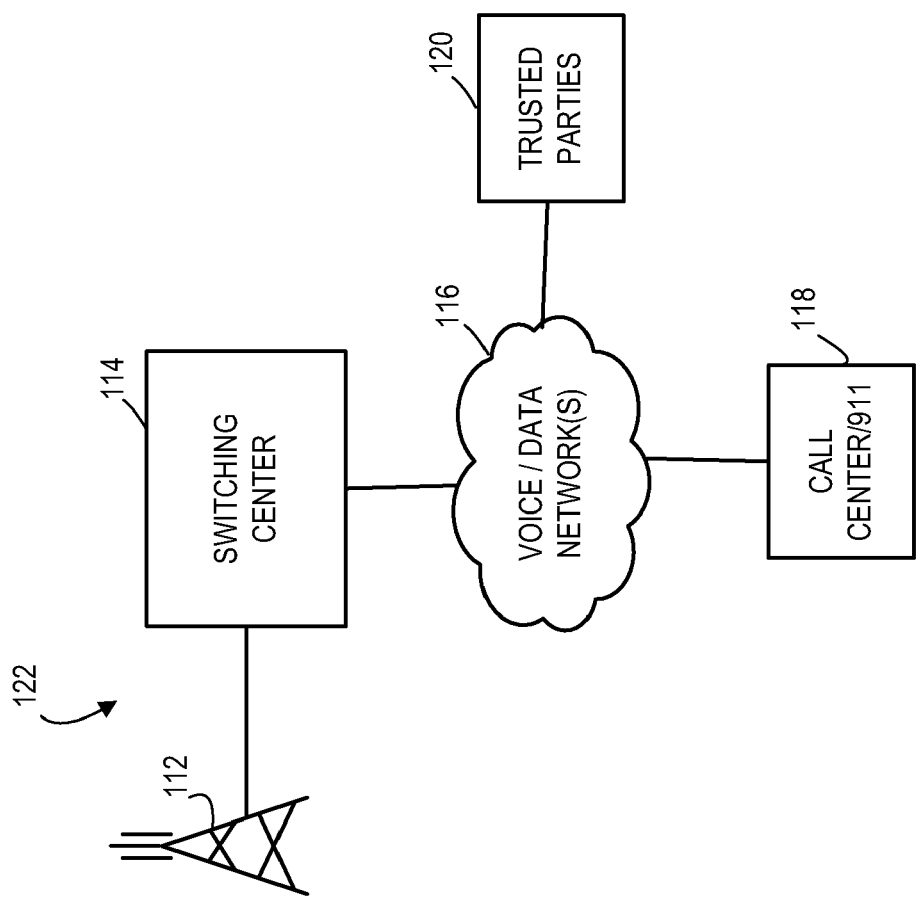
FIG. 1 is an example of an operating environment for various embodiments.
Figure 1:
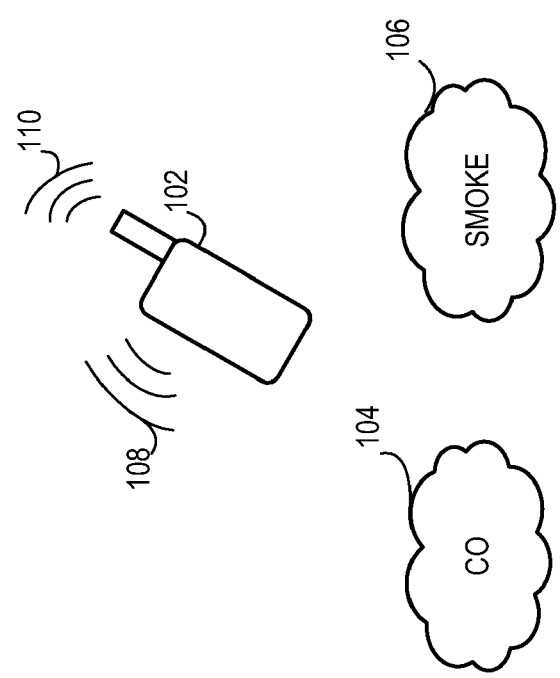

As shown in FIG. 1, a mobile communications device 102 may be present at a location where an environmental hazard is present, such as a carbon monoxide (CO) hazard 104 or a smoke hazard 106. The mobile communications device 102 in accordance with one or more embodiments may detect the presence of one or more of the hazards 104, 106 and then take action on behalf of the individual carrying the mobile communication device 102. For example, the mobile communications device 102 may generate a local alarm 108 such as sounding a ringer, displaying a message on a display screen, blinking lights, and/or vibrating. Additionally or alternatively, the mobile communications device 102 may generate an outbound wireless communication 110 to a mobile communications network 122, such as by originating a voice call, a text message, an electronic mail (email) message, and the like.

The mobile communications device 102 may be of various forms. For example, the mobile communications device 102 may be a cellular telephone that communicates through a conventional cellular telephone network. The mobile communications device 102 may be a mobile Internet device capable of communicating through Wi-Fi, Wi-Max or similar wireless data networks to carry conventional data messages or voice over Internet protocol. Furthermore, the mobile communications device may be a personal daily assistant device with communications abilities such as for cellular or Internet based communications networks.

The mobile communications network 122 channels the communication from the wireless communication device 102 to an intended destination such as an emergency/911 call center 118 and/or communications devices 120 of trusted parties such as friends and family. The mobile communications network 122 may include a base station 112 that directly exchanges the wireless signals with the mobile communications device 102. The base station 112 may communicate with a mobile switching center 114 that bridges the mobile communications network 122 to other networks 116 that carry voice and/or data such as public switched telephone networks, wide area data networks, the Internet, other mobile communications networks, and so forth.

During the outbound communication, the switching center 114 routes the communication to the appropriate downstream network 116 or directly to other mobile communications device on the same mobile communications network 122. Where the outbound communication is a text message or email, then the mobile communication network 122 may have no further duties with respect to the mobile communications device 102. However, if the outbound communication is a voice call, then the mobile communications network 122 may maintain an open line of communication between the mobile communications device 102 and the destination device 118, 120 until one of the devices terminates the call. The open line of communication may be unidirectional, where the mobile communications device 102 makes a voice announcement but is not intended to receive a voice response, or bidirectional where a voice response is returned to the mobile communications device 102.

The outbound communication that is provided to the emergency center 118 or device of trusted parties 120 may provide through text and/or speech a message pertaining to the hazard that is being experienced by the individual carrying the mobile communications device 102. For example, the message may be a text message that specifies the identify of the individual, a custom location entered by the individual in advance to identify the location, any location data obtained by the mobile communications device 102 such as geonavigational positioning system (GPS) data, and any details about the hazard such as the concentration of a poisonous gas that has been detected.

The type of hazard may also dictate the type of message and the destination for the message. For example, the mobile communications device may call a poison control center if a poison is detected while calling a fire station if smoke is detected. For detection of a poison such as CO, the mobile communications device may provide a message describing the CO detection and for smoke detection, may provide a message describing that smoke has been detected.

Figure 2:
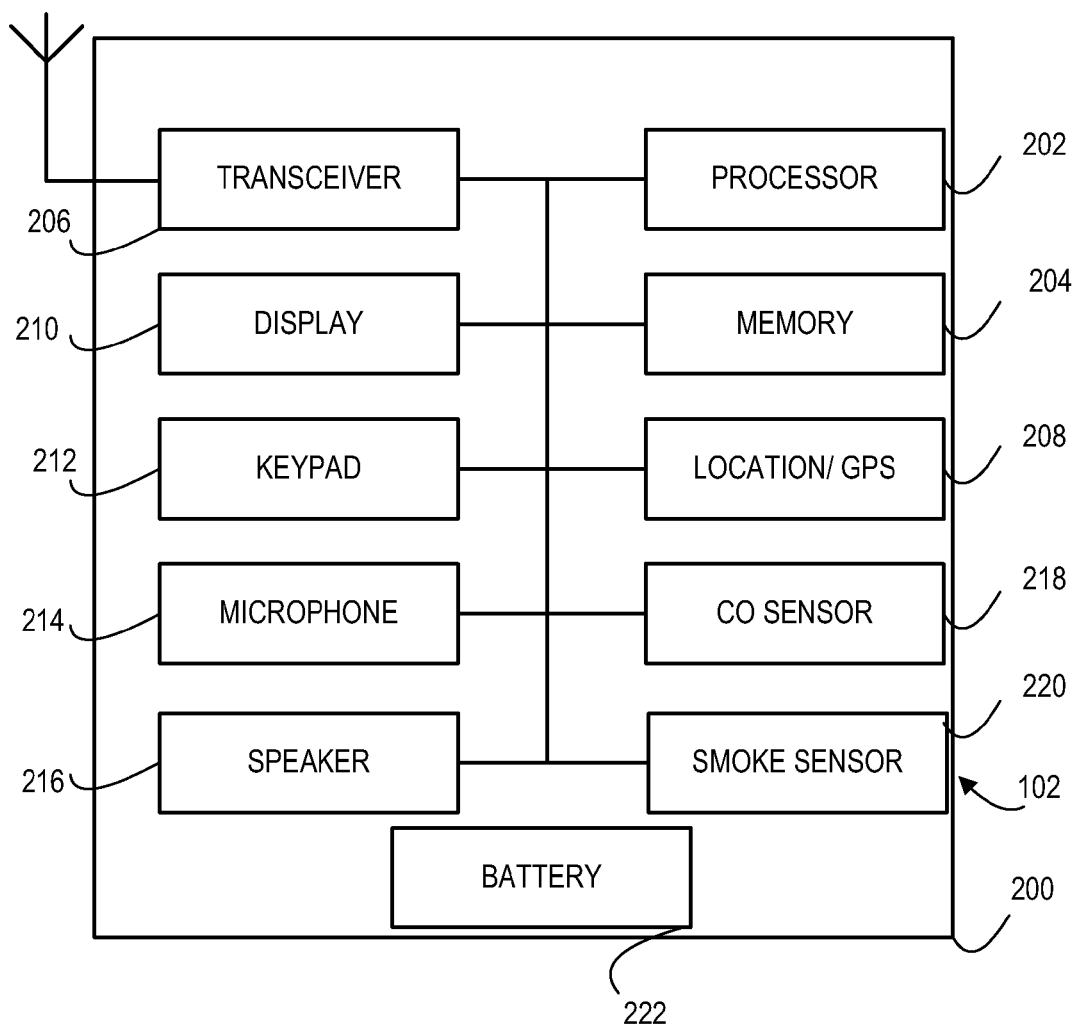
FIG. 2 shows an example of a mobile communications device according to various embodiments.

FIG. 2 shows an example of the mobile communications device 102 according to various embodiments. The mobile communications device 102 includes an outer body 200 that houses several internal components. These components include a processor 202 and memory 204. The processor 202 implements logical operations to provide any conventional functions of the mobile communications device 102. The processor may also implement logical operations such as those discussed below in relation to FIGS. 4-6 to monitor for the presence of environmental hazards, such as the hazards 104, 106, and then take an appropriate action when a hazard is detected. The processor 202 may be hard-wired digital logic, a general purpose programmable processor 202, an application specific processor, and any combination thereof.

The processor 202 may utilize the memory 204 to store data, to access programming instructions, and so forth. Examples of data that may be stored in memory 204 include thresholds for the sensing of hazards such as the threshold at which a poisonous gas concentration is dangerous. Other examples of data that may be stored in memory 204 include a home location and/or a custom location as entered by the user. The memory 204 may be volatile memory, non-volatile memory, or a combination thereof.

The processor 202 and/or memory 204 are examples of computer readable media which store instructions that when performed implement various logical operations. Such computer readable media may include various storage media including electronic, magnetic, and optical storage. Computer readable media may also include communications media, such as wired and wireless connections used to transfer the instructions or send and receive other data messages.

The processor 202 communicates with the other components, such as via a data bus, to provide for interaction with the user, handle incoming and outgoing communications, and monitor for the hazards. The processor utilizes a transceiver 206 to provide the wireless communications with the mobile communications network 122.

The processor 202 may communicate with various input and output components to interact with the user. The processor 202 may receive information from the user via input devices such as a keypad 212, including menu selections as well as identifications of locations. For example, the user may enter textual information describing the location of the home of the user to assist emergency personnel who may respond to an emergency message from the mobile communications device 102 by searching for the user at the home location. As another example, the user may enter textual information describing a custom location of the user, such as a hotel and room number so that emergency personnel can be directed to the correct room of the user at the hotel should a hazard exist. The processor 202 may store the textual information in memory 204.

In addition to entering textual information via the keypad 212, the user may enter verbal information by speaking into a microphone 214. This verbal information may describe the home location and/or the custom location of the user. The processor 202 may perform a digitization of the verbal information and store it in memory 204. The processor 202 may then retrieve the digitization and convert the digitization back to verbal information for sending through an outbound call, or send the digitization itself where the conversion takes place in the mobile communications network 122, in the event of a hazard that triggers the outbound call. The microphone 214 may also be used by the user during an outbound or inbound call to verbally communicate with a person or machine.

The processor 202 may provide information to the user via output devices such as a display screen 210. The display screen 210 may provide conventional information such as wireless signal strength, battery strength, in-call information such as elapsed time and the party of the communication, but may also provide additional information. The additional information may include such things as the active location to be announced in an outbound emergency communication, an indication that a hazard has been detected, and an indication that an action has been taken. Thus, the display device 210 may serve as one form of local alert to the user. This visual alert may be particularly significant for hearing impaired users who will not hear an audible alert but may see the display screen alert. The message may blink or otherwise have visual variation to increase the likelihood that a user may see the alert.

Figure 3:
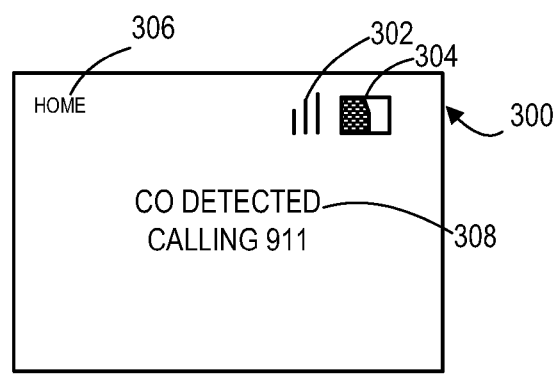
FIG. 3 shows an example of a display of the mobile communications device according to various embodiments.

An example of a display 300 of the display screen 210 is shown in FIG. 3. This display 300 includes a signal meter 302, battery meter 304, an active location indicator 306, and an alert message 308. In the example shown, the home location of the user that has been recorded in advance by the user is active, and a CO hazard has been detected. Furthermore, circumstances have resulted in the mobile communications device 102 placing a call to the 911 emergency services center 118.

As another example of an output device, a speaker 216 may receive an audio signal directed to the speaker by the processor 202 in order to provide audible information to the user. For example, the speaker 216 may produce conventional audible information such as a ringer or other audible cue regarding an incoming communication as well as the voice of a caller. However, the speaker 216 may produce additional information to provide a local alert to the user regarding the presence of a hazard. For example, the speaker 216 may sound an alarm, play a verbal message regarding the hazard, and so forth. As an option to supplement the audible alerts, a vibration generator may be included to provide the conventional vibration alert for incoming communications but may also provide a vibration alert for detected hazards.

The mobile communications device 102 may also include a location component 208, such as a GPS receiver or a triangulation receiver in order to determine a location of the mobile communications device 102. This location may be used as an alternative to, or in addition to any location that has been entered by the user for purposes of sending an outbound communication regarding the hazard.

In order to detect one or more hazards in the presence of the individual carrying the mobile communications device 102, one or more environmental hazard sensors are included within the body 200. In the example shown, both a CO sensor 218 and a smoke sensor 220 are included. Thus, in the example of FIG. 2, the processor 202 communicates with both the CO sensor 218 and the smoke sensor 220 to detect both types of hazards. Sensors for other environmental hazards, such as other types of poisonous gases, may also be included.

For use in the mobile communications device 102, it may be desirable that the environmental hazard sensors 218, 220 are a small size and have low power draw requirements. An example of a CO sensor, such as the sensor 218, is the gated metal oxide sensor produced by Applied Nanotech, Inc. of Texas, as disclosed in Sensors & Transducers e-Digest, Vol. 67, Issue 5, May 2006: Product News, which is incorporated by reference herein in its entirety. This sensor requires no heating and therefore has relatively low power consumption. An example of a smoke sensor, such as the sensor 220, is the HIS-07 Ionized Smoke Sensor manufactured by Henan Hanwei Electronics Co. of China, as disclosed at http://www.globalsources.com/gsol/I/Gas-sensor/p/sm/8834487616.htm, which is incorporated by reference herein in its entirety.

Regardless of the power consumption ratings of the sensors 218, 220 used, the processor 202 may only periodically utilize the sensors to sample the environment. In doing so, the processor 202 may ultimately conserve power being drawn by the environmental hazard monitoring process. Furthermore, as mentioned below, the mobile communications device 102 may have a button or menu selection for activating/deactivating sensing and/or may respond to verbal commands.

To provide the electrical power to the various components of the mobile communications device 102, a battery 222 may be included. The battery 222, such as a Lithium Ion, Nickel Cadmium, or Nickel Metal Hydride battery may be located within the body 200 or may have a dedicated body that attaches to an exterior surface of the body 200. In either case, the battery 222 maintains the portability of the mobile communications device 102 and thereby allows the mobile communications device 102 to be carried to any location by the individual while the functions including the monitoring for environmental hazards remain active.

Figure 4:
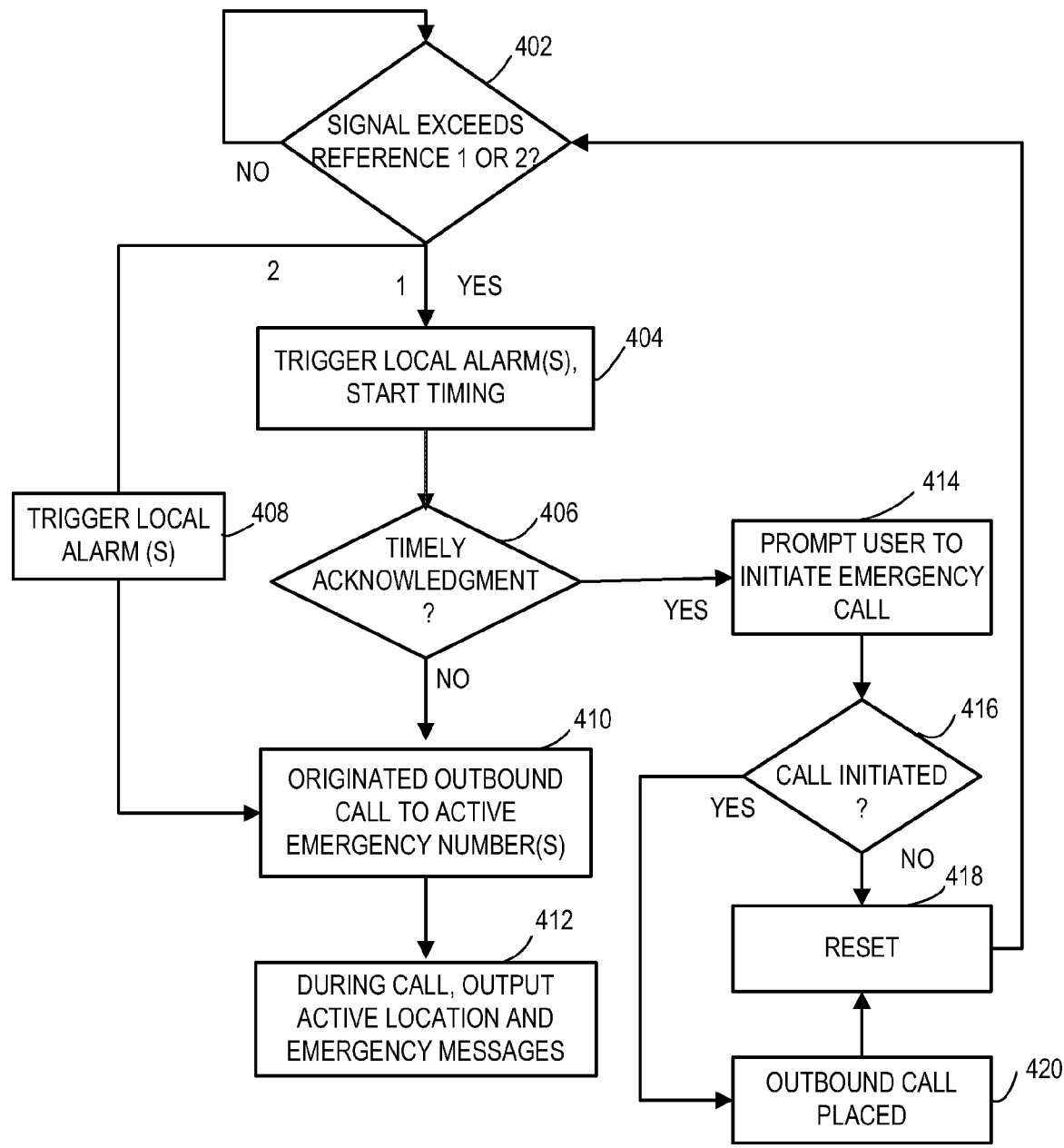
FIG. 4 shows an example of logical operations performed by the mobile communications device to detect hazards, alarm individuals, and originate emergency outbound calls according to various embodiments.

FIG. 4 shows an example of a set of logical operations that may be performed by the mobile communications device 102 to monitor for environmental hazards and to take action when a hazard is present. The operations begin by the processor 202 detecting whether a signal from an environmental sensor, such as the sensor 218, 220, exceeds one or more reference values at query operation 402. Multiple reference values may be set to dictate what actions should be taken. A low level reference point might indicate only a local alarm unless a certain amount of time passes without acknowledgement from the user. Furthermore, the low level may trigger more frequent sampling of the environment to determine whether a rise in the level has occurred. A high level reference point might indicate that an outbound call and a local alarm should be performed immediately.

If a low level reference is exceeded but not the high level reference, then logical operations proceed to alarm operation 404. Here, the processor 202 triggers one or more available local alarms, such as a ringer, a blinking display, and/or a vibration to alert the individual to the hazard. Also at this point, the processor 202 may start a timer that will be used to determine whether an acknowledgement from the user is received within a pre-defined period of time. The acknowledgement may be the individual pressing a key on the keypad to indicate that the alert has been noticed. If the acknowledgement is not received, then the circumstances may be that the individual has simply not noticed the alert or that the individual has become incapacitated by the hazard. In either case, more drastic actions may be necessary.

At query operation 406, the processor 202 determines whether the individual has acknowledged the alert before the pre-defined period of time has lapsed. If the acknowledgement has been timely received, then the processor 202 may prompt the user to initiate an emergency call at output operation 414. The prompt may be a variety of outputs such as a verbal announcement to the individual, a textual prompt displayed on the screen, or a patter of blinking, ringing, or vibrating that is known to the individual to be such a prompt.

The processor 202 detects whether the user has selected to initiate the emergency call at query operation 416, such as by issuing a voice command or touching a particular key on the keypad 212 to initiate the call. If the user has not chosen to initiate the call, such as because the hazard is minimal or it was a false alarm, then the mobile communications device 102 may reset back to a monitoring mode at reset operation 418. If the call is initiated by the user, then the mobile communications device 102 places the outbound communication at outbound operation 420, such as a standard voice call between the individual and a 911 service, and then the mobile communications device resets to the monitoring mode.

Returning to query operation 406, if the acknowledgement is not timely, then the processor 202 proceeds by originating an outbound communication to the active emergency numbers at outbound operation 410. Then, during the call or other communication, the processor 202 provides the active location message and any additional emergency messages at message operation 412. As previously discussed, the active location message may be a message regarding the home of the user or a custom message defining a current short-term location of the user. Additionally, should the embodiment not provide for such a location message or if the user has not activated a location message, then no location may be provided during the communication. Furthermore, the emergency messages may include specifics about the hazard that has been detected, such as the type of hazard and the hazard's severity.

Returning to query operation 402, if the high level reference has been exceeded, then the processor 202 may immediately trigger the local alarm(s) in an attempt to capture the attention of the individual at operation 408. The processor may also immediately originate the outbound communication at outbound operation 410 and then provide the locations and messages via the outbound communication at message operation 412.

Figure 5:
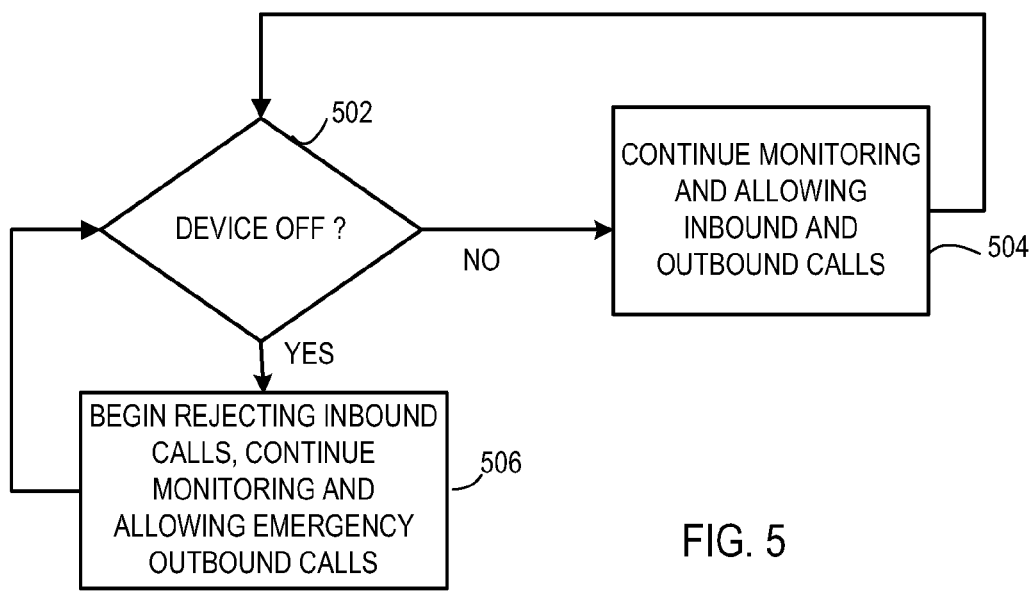
FIG. 5 shows an example of logical operations performed by the mobile communications device to enter a powered off state according to various embodiments.

FIG. 5 shows an example of logical operations that may be performed by the mobile communications device 102 concurrently with the logical operations of FIG. 4, to allow the user to power down the mobile communications device 102 while retaining the monitoring function. At query operation 502, the processor 202 detects whether the user has selected an option to power off the mobile communications device 102. If not, then the processor 202 continues to monitor for environmental hazards and allows inbound and outbound communications such as voice calls, text messages, and the like at a first device state 504. If the processor 202 detects that the user has selected an option to power down, then the processor 202 may begin rejecting inbound communications while continuing to monitor and allow outbound emergency calls at a second device state 506.

The processor 202 may implement the first device state 504 and second device state 506 by controlling which components remain operational and which are effectively shut down. For example, in the first device state 504, the processor 202 may remain attentive to all input components, continue to use all output components, and maintain the transceiver 206 in a fully operational mode with connectivity maintained with a base station 112. As another example, in the second device state 506, the processor 202 may remain attentive to only the power button of the keypad 212 and the environmental hazard sensor 218, 220. In this second device state 506, the processor 202 may either power down the transceiver 206 and then power the transceiver up again upon detecting that an emergency outbound call is needed or may maintain the transceiver in a fully operational mode but immediately reject incoming communications from the base station 112.

Variations on the states shown in FIG. 5 may also be implemented. For example, there may be a user selectable option to defeat the environmental hazard monitoring while maintaining other conventional functions of the mobile communications device 102. One situation where this might be desirable would be sitting nearby a campfire where smoke and CO are likely to be present, but the individual carrying the phone 102 is aware of the campfire and does not want to be alerted. Another user selectable option may be to power down all functions including the environmental hazard monitoring such as to provide maximum battery preservation.

Figure 6:
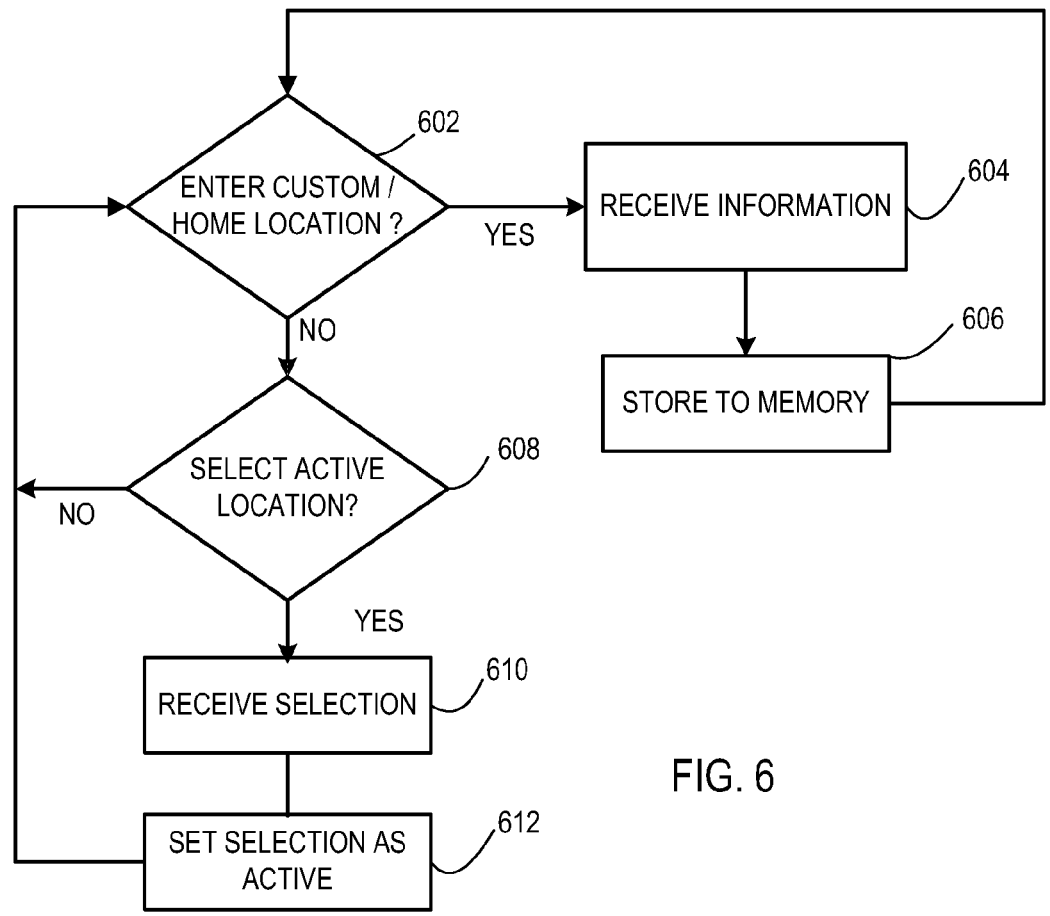
FIG. 6 shows an example of logical operations performed by the mobile communications device to receive and activate custom location messages according to various embodiments.

FIG. 6 shows an example of a set of logical operations that may also be performed concurrently with the logical operations of FIG. 4. These logical operations allow the individual carrying the mobile communications device 102 to specify the information that will identify the location of the individual. In this example, the individual may specify both a home location and a custom location. The home location may be set and then not changed until the individual moves to a new home. The custom location may be frequently changed, as the individual moves from place to place. The information specified may be as specific as the individual prefers, such as specifying a particular hotel room as the custom location. Accordingly, when the location information is provided via an outbound emergency communication, the recipient of the information will have a more precise idea of where the individual and the hazard are located.

At query operation 602, the processor 202 detects whether the user has chosen to enter a custom or home location. If so, the processor 202 receives the information via an input device such as the keypad 212 or microphone 214 at reception operation 604. The processor 202 then stores the received location information to memory 204 at storage operation 606. The location information is stored in association with whether the location information is for the home location or the custom location so that each one is individually accessible by the processor 202.

If the user is not entering the location information, then at query operation 608 the processor 202 detects whether the user is attempting to select which location is the active one. While the user is at home, the user will select that the home location is active so that the processor 202 will access the home location information from memory 204 when providing information during the outbound emergency communication. While the user is away from home, the user will select that the custom location is active so that the processor 202 will access the custom location information from memory 204 when providing information during the outbound emergency communication. The processor 202 receives the selection, either home or custom, at reception operation 610 by the user entering information via an input component. The processor 202 then sets the selection as active at selection operation 612, such as by flagging in memory 204 whichever location information should be provided.

Accordingly, as discussed above, an individual carrying the mobile communications device 102 according to various embodiments may benefit from continued monitoring for environmental hazards by the mobile communications device 102 as the individual moves from place to place. The individual may further benefit from the mobile communications device 102 taking some action relative to environmental hazards when appropriate, such as producing local alarms and/or originating outbound emergency communications.

While embodiments have been particularly shown and described, it will be understood by those skilled in the art that various other changes in the form and details may be made therein without departing from the spirit and scope of the invention.

What is claimed is:

1. A mobile communications device, comprising:
    a portable body;
    a transceiver within the portable body that sends and receives wireless communication signals to a mobile communications network;
    an environmental hazard sensor within the portable body that produces a signal value based on sensing at least one characteristic of an environmental hazard;
    a processor that interacts with the transceiver to establish communications with the mobile communications network and that interacts with the environmental hazard sensor to analyze the signal value against a reference and to originate an outbound communication to the mobile communications network upon detecting that the signal value exceeds the reference;
    a portable power source that is affixed to the portable body and that provides electrical power to the transceiver, the environmental sensor, and the processor; and
    an input component within the portable body that receives user input, and wherein the processor interacts with the input component to receive and act upon the user input;
    and wherein the processor maintains a home location and provides an indicator of whether the home location or a custom location is active, and wherein the processor receives the user input via the input component to activate the home location or the custom location.

2. The mobile communications device of claim 1, wherein the environmental hazard sensor comprises at least one carbon monoxide sensor.

3. The mobile communications device of claim 1, wherein the environmental hazard sensor comprises at least one smoke detector.

4. The mobile communications device of claim 1, wherein the processor periodically interacts with the environmental hazard sensor to analyze the signal value against the reference.

5. The mobile communications device of claim 1, wherein the processor implements an off mode during which incoming communications from the mobile communications network are not accepted, the environmental hazard sensor continues to produce the signal value, and the processor continues to analyze the signal value against the reference and originate the outbound communication to the mobile communications network upon detecting that the signal value exceeds the reference.

6. The mobile communications device of claim 1, further comprising:
    an output component within the portable body that produces an output that is perceivable by a user, and wherein the processor interacts with the output component to produce the perceivable output.

7. The mobile communications device of claim 6, wherein the processor instructs the output component to produce an alarm as the perceivable output upon detecting that the signal value exceeds a local alarm reference that is lower than the reference that causes the outbound communication to be originated.

8. The mobile communications device of claim 1, wherein the processor instructs the output component to produce an alarm as the perceivable output upon detecting that the signal value has exceeded the reference and then originates the outbound call if no user input via the input component is received within a set amount of time after having produced the alarm.

9. The mobile communications device of claim 1, wherein the output component is at least one of a display screen and a speaker and wherein the input component is at least one of a keypad and a microphone.

10. The mobile communications device of claim 1, wherein the processor receives user input specifying a custom location from the input component and outputs the custom location during the outbound communication to the mobile communications network.

11. The mobile communications device of claim 1, further comprising a location detector within the body and wherein the processor receives information from the location detector that specifies a current location and outputs the current location in addition to the home location or the custom location during the outbound communication to the mobile communications network.

12. The mobile communications device of claim 1, further comprising a location detector within the body and wherein the processor receives information from the location detector that specifies a current location and outputs the current location during the outbound communication to the mobile communications network.

13. A method of alerting to a hazardous environment using a mobile communications device present within the hazardous environment, comprising:
    producing via an environmental hazard sensor within the mobile communications device a signal value;
    determining via the mobile communications device whether to originate an outbound communication to a mobile communications network on the basis of the signal value;
    originating the outbound communication from the mobile communications device when the outbound communication is determined to be appropriate;
    providing information stored at the mobile communications device regarding a location of the hazardous environment during the outbound communication; wherein the information stored at the mobile communications device comprises at least one of a home location and a custom location; and
    receiving a selection from a user of the home location or the custom location in advance of determining to originate the outbound communication.

14. The method of claim 13, wherein determining whether to originate an outbound communication comprises generating a local alarm via the mobile communications device and determining whether user input to acknowledge the alarm is received within a set amount of time.

15. The method of claim 13, further comprising detecting at the mobile communications device a current location and wherein the information provided during the outbound communication comprises the current location.

16. A non-transitory computer readable medium containing instructions encoded thereon that perform acts comprising:

producing via an environmental hazard sensor within a mobile communications device a signal value;

determining via the mobile communications device whether to generate an alarm on the basis of the signal value;

determining whether to originate an outbound communication to a mobile communications network if no acknowledgement to the alarm is received at the mobile communications device within a set period of time;

originating the outbound communication from the mobile communications device to the mobile communications network upon determining that no acknowledgement has been received at the mobile communications device within the set period of time, providing information stored at the mobile communications device regarding a location of the hazardous environment during the outbound communication, wherein the information comprises at least one of a home location and a custom location; and receiving a selection from a user of the home location or the custom location in advance of determining to originate the outbound communication.

* * * * *